United States Patent [19]

Schrock

[11] 4,021,429

[45] May 3, 1977

[54] SYNTHESIS OF ETHYLENICALLY UNSATURATED COMPOUNDS FROM ESTERS OR AMIDES

[75] Inventor: Richard Royce Schrock, Wilmington, Del.

[73] Assignee: E. I. Du Pont de Nemours and Company, Wilmington, Del.

[22] Filed: July 24, 1975

[21] Appl. No.: 599,015

[52] U.S. Cl. .................. 260/293.51; 260/583 H; 260/614 R
[51] Int. Cl.² ................................ C07D 295/02
[58] Field of Search .......... 260/293.51, 583 H, 614

[56] References Cited
OTHER PUBLICATIONS

Morrison et al., "Organic Chemistry, 2nd Ed.," Allyn and Bacon, Inc., Boston (1966), pp. 870–871.

*Primary Examiner*—G. Thomas Todd
*Attorney, Agent, or Firm*—Anthony P. Mentis

[57] ABSTRACT

Certain hydrocarbylidene-niobium or -tantalum complexes react with esters or N,N-disubstituted amides to produce ethylenically unsaturated compounds. Exemplary is the reaction of trineopentyl(neopentylidene)-tantalum with ethyl acetate to produce 2-ethoxy-4,4-dimethyl-2-pentene:

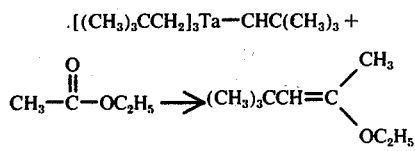

12 Claims, No Drawings

SYNTHESIS OF ETHYLENICALLY UNSATURATED COMPOUNDS FROM ESTERS OR AMIDES

BACKGROUND OF THE INVENTION

1. Field of the Invention

This invention is the reaction of certain hydrocarbylideneniobium or hydrocarbylidenetantalum complexes with esters or N,N-disubstituted amides to produce ethylenically unsaturated compounds.

2. Prior Art

It is known to react a phosphonium ylid with an aldehyde or ketone to give an olefin; A. W. Johnson "Ylid Chemistry," pp. 132–192 (Academic Press 1966), but no reference appears to exist with respect to the use of a niobium or tantalum complex for such reaction.

SUMMARY OF THE INVENTION

The invention is the process of reacting a metal compound of the formula

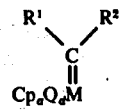

in which
- Cp is a $\pi$-cyclopentadienyl group having up to one alkyl substituent of 1–10 carbons;
- Q is alkyl of 1–10 carbons, aralkyl of 7–10 carbons or diarylmethyl of 13–21 carbons in which the $\beta$-carbon is not bonded to hydrogen;
- M is niobium or tantalum;
- $R^1$ and $R^2$ individually are hydrogen, tertiary alkyl of 4–10 carbons or aryl of 6–10 carbons;
- $a$ is 0 or 2;
- $d$ is 1 or 3; and
- $a$ plus $d$ equals 3;

with an organic carbonyl compound of the group consisting of an ester of a carboxylic acid and an N,N-disubstituted amide of a carboxylic acid, said carbonyl compound being free of Zerewitinoff-active hydrogen and any multiple bond present other than that in the carbonyl group being a carbon to carbon multiple bond or a multiple bond contained in an aromatic heterocyclic ring, at a temperature in the range of 0°–250° C, and in the substantial absence of oxygen and moisture to produce an ethylenically unsaturated compound. As is known, a compound that reacts with a Zerewitinoff reagent to produce methane is considered to have Zerewitinoff-active hydrogen.

The reaction can be exemplified by the equation

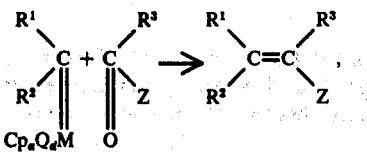

where $Z=OR^4$ or $NR^5R^6$. The fate of the $Cp_aQ_dM$ moiety is not known.

The reaction is a broad one in that any ester or amide of a carboxylic acid, of whatever size or complexity, will work in the reaction so long as it conforms to the criteria stated above. The process produces vinyl ethers from esters and vinyl amines from amides.

So long as the carbonyl compound as a whole satisfies the criteria mentioned, $R^3$ can be hydrogen, $OR^4$, or any organic group bonded through carbon, and $R^4$, $R^5$, and $R^6$ can be any organic group bonded through carbon. Such organic groups include alkyl, alkenyl, alkynyl, cycloalkyl, cycloalkenyl or aryl, and groups containing more than one such structure, as alkylcycloalkyl, alkaryl, aralkyl and the like. Since $R^3$ can contain double and triple bonds, the process can produce not only monoethylenically unsaturated compounds but also dienes, enynes and the like. $R^5$ and $R^6$ can be the same or different, and together can be a divalent organic group.

The groups can also contain one or more hetero atoms and can therefore include substituents such as hydrocarbyloxy, hydrocarbylthio and dihydrocarbylamino, as for example, oxaalkyl, thiaalkyl, azaalkyl and alkenyl, alkynyl, cycloalkyl and aryl corresponding containing a hetero atom. Thus the groups can contain or be composed of units derived, for example, from tetrahydrofuran, tetrahydrothiophene, piperidine, furan, thiophene, or pyridine. In any units derived from piperidine or other cyclic secondary amines there would be no hydrogen on the nitrogen, e.g., as in 2-piperidinoethyl. For convenience in naming, groups such as alkyl, alkenyl, cycloalkyl and aryl containing one or more hetero atoms in the carbon skeletons can be designated here as heteraalkyl, heteraalkenyl, heteracycloalkyl and heteraaryl groups, respectively. Examples, also respectively, are 2-methoxyethyl, 2-vinyloxyethyl, 3-tetrahydrothienyl, and 4-pyridyl. Substituents also include halo groups, i.e., fluoro, chloro, bromo, and iodo. Any halo substituent should be on a carbon separated from the carbonyl carbon by at least one other carbon.

Because of availability or reactivity preferred esters have the formula

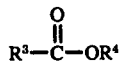

where $R^3$ is hydrogen, alkoxy of 1–8 carbons, alkyl of 1–8 carbons, alkenyl of 2–8 carbons, aryl of 6–12 carbons or aralkyl of 7–12 carbons, each having up to one substituent of halo, alkoxy of 1–6 carbons, alkylthio of 1–6 carbons or dialkylamino each alkyl having 1–6 carbons; and $R^4$ is alkyl of 1–8 carbons. Most preferably $R^3$ is free of substituents.

Amides which are presently preferred for reasons of availability or reactivity have the formula

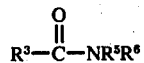

where $R^3$ is as defined above and $R^5$ and $R^6$ are the same or different and individually are alkyl of 1–8 carbons, alkenyl of 2–8 carbons, aryl of 6–12 carbons or aralkyl or 7–12 carbons, each having up to one substituent of halo, alkoxy of 1–6 carbons, alkylthio of 1–6 carbons or dialkylamino each alkyl having 1–6 carbons, with the proviso that the $R^5$ groups can be joined together to form an alkylene group of 3–8 carbons.

Most preferred are compounds where $R^5$ and $R^6$ are alkyl of 1–8 carbons.

Representative carbonyl compounds include ethyl acetate, methyl 4-cyclohexylbenzoate, isobutyl octanoate, methyl methacrylate, cyclopentyl undecylenate, ethyl hexadecanoate, 3-chloropropyl 2-tetrahydrofurancarboxylate, hexyl 4-biphenylcarboxylate, 2-dipentylaminoethyl formate, phenyl 6-ethylthiohexanoate, isopropyl 3-hexynoate, ethyl 4-bromo-1-naphthoate, propyl 3-ethoxybenzoate, 2-ethylhexyl 2-ethylthiopropionate, ethyl 3-quinolinecarboxylate, diethylisovaleramide, N-benzoylpiperidine, N,N-dipentyl-p-toluamide, N-(4-fluorobutanoyl)pyrrolidine, N,N-diisopropyl-2-iodobenzamide, N,N-dibutylhexyloxyacetamide, N,N-dimethyl-4-pyridinecarboxamide, N,N-dihexyltetradecanamide, N,N-dimethyl-1-methyl-2-naphthalenecarboxamide, N,N-diethyl-4-diethylaminobenzamide, N,N-bis(2-methoxyethyl)acetamide, N,N-dipentyl-4-heptenamide, diethylpropiolamide, ethyl dimethylcarbamate, and the like.

The process can be carried out in the presence or absence of a solvent. Useful solvents include ethers, such as ethyl ether, tetrahydrofuran, dioxane, 1,2-dimethoxyethane, and 2-methoxyethyl ether, and hydrocarbons such as pentane, hexane, heptane, cyclohexane, benzene, toluene, and petroleum ether. When an excess of carbonyl compound is used and the compound is a suitable liquid, the excess carbonyl compound can function as solvent. The niobium- and tantalum-containing starting materials are usually prepared in ether or hydrocarbon solvents, and if desired, solutions thus obtained can be used directly in the present process without isolation of the starting material.

The reactant ratio, temperature, and time can be varied, depending on the nature of the reactants.

Niobium- and tantalum-containing starting materials in which $a$ is 0 and $d$ is 3 can be written as $Q_3M=CR^1R^2$. When such starting material is reacted with an ester the reaction requires about 1 to 2 hours at 25° C with a 1:1 ratio but the required time can be decreased by raising the temperature. Carbonate esters appear to be less reactive than the simple alkanoates like ethyl acetate, and times of the order of 16 hours at about 100° C or higher are required for completion of the reaction.

When one of the reactants is a carboxamide other than a formamide, the reaction requires about 2 days at 25° C. It can be speeded up by operating at higher temperatures within the stated temperature range. At least 2 moles of carbonyl compound per mole of organometallic compound should be used, both to increase the rate of reaction and because one mole of carbonyl compound appears to complex with a niobium-or tantalum-containing by-product. Higher mole ratios increase the rate.

Metal-containing starting materials which $a$ is 2 and $d$ is 1, which can be formulated as $Cp_2QM=CR^1R^2$, react more slowly than the $Q_3M=CR^1R^2$ type, and the latter are therefore preferred. For example, several hours at temperatures averaging higher than 50° may be required for carboxylic esters and for carboxamides. Again, higher carbonyl-organometallic ratios, e.g., from about 10:1 to 100:1 or even higher, help speed up the process.

In all the foregoing embodiments, pressure is not a particularly critical variable. Usually, the process is conducted at atmospheric pressure for convenience. When the process is conducted near or above the boiling point of the carbonyl compound, it is customary to operate at the autogeneous pressure developed in a closed system. The course of the reaction can usually be followed by observing the precipitation of the niobium- or tantalum-containing by-product.

The niobium- or tantalum-containing starting materials can be prepared according to the procedures set out in copending application Ser. No. 570,259 now U.S. Pat. No. 3,988,332 filed on or about Apr. 21, 1975, in the name of Richard R. Schrock. That application discloses three methods for preparing starting materials of the formula $$Q_aM=CR^1R^2$$

where $a$ is zero and $d$ is 3 as follows.

In the first method, a trihydrocarbylmetal dichloride, $Q_3MCl_2$, such as trineopentyltantalum dichloride or trineopentylniobium dichloride is reacted with 2 moles of a hydrocarbyllithium compound in which the hydrocarbyl group corresponds to the hydrocarbylidene group in the product:

$$(C_5H_{11})_3MCl_2 + 2LiCHR^1R^2 \rightarrow (C_5H_{11})_3M=CR^1R^2 \\ + CH_2R^1R^2 + 2LiCl \tag{1}$$

In the second method, 4 moles of a hydrocarbyllithium, QLi, such as neopentyllithium are reacted with one mole of a hydrocarbyltantalum tetrachloride or hydrocarbyl-niobium tetrachloride in which the hydrocarbyl group corresponds to the hydrocarbylidene group in the product:

$$4C_5H_{11}Li + Cl_4MCHR^1R^2 \rightarrow (C_5H_{11})_3M=CR^1R^2 + \\ C_5H_{12} + 4LiCl \tag{2}$$

The ultimate source of tantalum or niobium in each of these three processes is tantalum pentachloride or niobium pentachloride. In the third method, a trihydrocarbyl(hydrocarbylidene)tantalum compound such as trineopentyl(neopentylidene)tantalum, is prepared directly from $TaCl_5$ by reacting it with 5 moles of an appropriate hydrocarbyl Grignard reagent such as neopentylmagnesium chloride:

$$TaCl_5 + 5C_5H_{11}MgCl \rightarrow (C_5H_{11})_3Ta=CHC(CH_3)_3 \\ + 5MgCl_2 + C_5H_{12} \tag{3}$$

The corresponding niobium compounds can be similarly prepared from $NbCl_5$.

Starting materials of the formula $$Cp_2QM=CR^1R^2$$

where $a$ is 2 and $d$ is 1 are prepared by reacting an appropriate dihydrocarbylmetal trihalide with 2 moles of cyclopentadienylthallium:

$$2CpTl + Cl_3M(CHR^1R^2)_2 \longrightarrow \underset{Cl}{Cp_2M=CR^1R^2} \tag{4}$$
$$+ CH_2R^1R^2 + 2TlCl.$$

The product of the equation (4) can then be reacted with an appropriate hydrocarbyllithium, or preferably a diamine complex thereof, for example, according to equation (5):

$$\underset{Cl}{Cp_2M=CR^1R^2} + (C_6H_5)_2CHLi \longrightarrow \underset{(C_6H_5)_2CH}{Cp_2M=CR^1R^2} \tag{5}$$
$$+ 2LiCl$$

Examples of alkyl groups that can be substituents in the cyclopentadienyl ring are methyl, ethyl, isopropyl, t-butyl, hexyl, octyl, and decyl. Because of the commercial availability of cyclopentadiene and methylcylopentadiene, the cyclopentadienyl and methylcyclopentadienyl groups are preferred. Examples of suitable groups are thus cyclopentadienyl, methylcyclopentadienyl, ethylcyclopentadienyl, isopropylcyclopentadienyl, t-butylcyclopentadienyl, hexylcyclopentadienyl), octylcyclopentadienyl and decylcyclopentadienyl.

Examples of Q are methyl, neopentyl, 2,2,4,4-tetramethyl-3-pentyl, benzyl, p-ethylbenzyl, naphthylmethyl, $\beta,\beta$-dimethylphenethyl ("neophyl"), diphenylmethyl, and ditolylmethyl. A preferred class of Q groups comprises alkyl and aralkyl and most preferably Q is methyl, neopentyl or benzyl.

Examples of $R^1$ and $R^2$ are tertiary butyl, tertiary pentyl, tertiary hexyl, tertiary heptyl, tertiary octyl, tertiary nonyl and tertiary decyl.

"Aryl" and "ar" are used herein to denote a radical derived from a hydrocarbon having as its only unsaturation aromatic unsaturation in six-membered carbocyclic rings by removal of a hydrogen atom from a carbon atom in such an aromatic ring.

Examples of aryl groups are phenyl, 1- and 2-naphthyl, o-, m- and p-tolyl, ethylphenyl, butyl-phenyl, xylyl, and trimethylphenyl.

Exemplary of the preparation of these compounds are the following, in which the reaction is carried out in an atmosphere of dry nitrogen.

EXAMPLE A

Trineopentyl(neopentylidene)tantalum

A. A solution of 0.05 g of trineopentyltantalum dichloride and 0.17 g of neopentyllithium in 4 ml of pentane was allowed to stand at room temperature for 24 hr in a glass vessel wrapped in foil. (In later experiments it was found that the foil wrapping was unnecessary.) The lithium chloride that had precipitated was separated by filtration, and the filtrate was allowed to stand for another 24 hr at room temperature. No more solid precipitated during this time. Volatile materials were removed under reduced pressure to give trineopentyl(neopentylidene)tantalum, $(C_5H_{11})_3Ta=C_5H_{10}$, as an orange crystalline solid.

An $^1H$ nmr of the product in $C_6D_6$ showed four singlets in the ratio 1:9:27:6 at $\tau 8.09$ (1), $\tau 8.57$ (9), $\tau 8.85$ (27), and $\tau 9.16$ (6).

B. The foregoing procedure was essentially repeated (24-hr reaction period) with double quantities of materials to give 0.85 g (85%) of $(C_5H_{11})_3Ta=C_5H_{10}$. The product was combined with the product from part A, and the mixture was heated in a sublimation apparatus at 80° C/0.5$\mu$. The crystals thus obtained on the cold finger had the same appearance and the same $^1H$ nmr as the original product. A mass spectrum showed a peak at m/e 464.

C. A solution of 5.15 g of $(C_5H_{11})_3TaCl_2$ and 1.75 g of $C_5H_{11}Li$ in 50 ml of pentane was allowed to stand at room temperature for 8 hours, and the lithium chloride that precipitated was removed by filtration. When the volume of the filtrate was reduced to about 5 ml under reduced pressure without heating, orange crystals precipitated; they redissolved when the mixture was allowed to warm to room temperature. The mixture was filtered, and the filtrate was kept overnight at −30° C. No crystals appeared. The volume of the solution was reduced from 6 ml to 4 ml, and the solution was allowed to stand overnight again at −30° C. The orange crystals of $(C_5H_{11})_3Ta=C_5H_{10}$ that appeared were separated by filtration; yield 2.5 g. Removal of the rest of the solvent under reduced pressure gave an additional 1.8 g of product. The total yield was 84%.

| Anal. calcd. for $C_{20}H_{45}Ta$: | | | | | | |
|---|---|---|---|---|---|---|
| | C, 51.72; | H, 9.33, | Ta, 38.95; | mol wt, 464 |
| Found: | C, 51.39; | H, 9.31; | Ta, 41.22; | mol wt, 472 |
| | 51.09 | 9.24 | 42.77 | |
| | 50.86 | 9.22 | | (cryoscopic in benzene) |

EXAMPLE B

Trineopentyl(neopentylidene)tantalum $[(CH_3)_3CCH_2]_3Ta=CHC(CH_3)_3$

A mixture containing the Grignard reagent prepared from magnesium metal and 160 g of neopentyl chloride in about one liter of ethyl ether was added rapidly with stirring to 107 g of tantalum pentachloride and about 1 liter of ethyl ether. The mixture was stirred for 1 hour and filtered, and all volatile material was removed from the filtrate under reduced pressure. The residue was extracted with about 200 ml of pentane, and the filtered extract was evaporated under reduced pressure. The residue was volatilized in a sublimation apparatus at 100° C/1$\mu$ to give a total of 75 g (50%; 3 crops) of $(C_5H_{11})_3Ta=C_5H_{10}$ as deep-orange nugget-like crystals; mp 71° C (sealed tube).

EXAMPLE C

Trineopentyl(benzylidene)tantalum

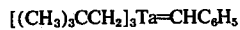

A solution of 2.6 g of $(C_5H_{11})_3TaCl_2$ in 100 ml of hexane was cooled to −78° C, and a solution of 2.4 g of benzyl (N,N,N',N'-tetramethylethylenediamine)lithium in 30 ml of toluene was added dropwise over 1 hour with rapid stirring. The mixture was warmed to 25° C, stirred for an additional hour, and filtered, and volatile materials were removed from the deep-orange filtrate under reduced pressure, to give an orange residue that contained trineopentyl(benzylidene)tantalum.

If 4-methylbenzyllithium or a suitable diamine complex thereof is used in place of benzyllithium in essentially the procedure above, trineopentyl(4-methylbenzylidene)tantalum, $(C_5H_{11})_3Ta=CHC_6H_4CH_3$, will be formed. If 1-naphthylmethyllithium or a complex thereof is used, the product will be trineopentyl(1-naphthylmethylene)tantalum, $(C_5H_{11})_3Ta=CHC_{10}H_7$.

EXAMPLE D

Dicyclopentadienyl(methyl)methylene)niobium

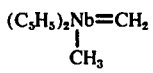

a. $(C_5H_5)_2Nb(CH_3)_3$ was prepared by stirring a mixture of 0.42 g of $(CH_3)_3NbCl_2$, 1.08 g of $C_5H_5Tl$, and about 20 ml of toluene for 1 hour at room temperature. TlCl was separated by filtration, the filtrate was evaporated in vacuo nearly to dryness, the residue was triturated with pentane, and the mixture was filtered to give 0.28 g of greenish crystals.

$^1$H nmr ($\tau$, $C_6D_6$): ~5.3 (10, s), ~9.7 (6, s), ~9.8 (3, s).

b. $[(C_5H_5)_2Nb(CH_3)_2]^+BF_4^-$ was prepared by mixing dichloromethane solutions of 0.34 g of $(C_5H_5)_2Nb(CH_3)_3$ and 0.42 g of $(C_6H_5)_3C^+BF_4^-$, whereupon the product precipitates as a yellow solid; yield 0.31 g. $(C_6H_5)_3CCH_3$ was identified in the residue from the filtrate.

$^1$H nmr ($\tau$. $CD_3CN$): 3.92 (10, s), 9.23 (6, s).

C. $[(C_5H_5)_2Nb(CH_3)_2]^+BF_4^-$ (0.31 g) in ca. 10 ml of tetrahydrofuran was treated with 0.08 g of $(CH_3)_3P=CH_2$. All solids dissolved. The solvent was removed in vacuo and the residue was extracted with pentane. This gave a pentane solution of thermally unstable $(C_5H_5)_2Nb(CH_3)=CH_2$.

SPECIFIC EMBODIMENTS OF THE INVENTION

In the following illustrative examples, all parts are by weight and all degrees are centigrade unless otherwise stated. All operations at least up to the isolation of the products were conducted in an atmosphere of dry nitrogen.

EXAMPLE 1

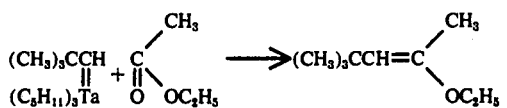

Equivalent amounts of $(C_5H_{11})_3Ta=C_5H_{10}$ and ethyl acetate were dissolved in pentane, and the solution was stirred for 1.5 hr at room temperature. The pale-yellow solid that had precipitated was removed by filtration, and the filtrate was shown by mass spectroscopy to contain a mixture of the cis and trans isomers of 2-ethoxy-4,4-dimethyl-2-pentene.

Other esters can be used in place of ethyl acetate to give ethylenically unsaturated products. Thus, butyl β-ethylthiopropionate will give 4-butoxy-2,2-dimethyl-7-thia-3-nonene; methyl 4-diethyl-aminobenzoate will give 1-(4-diethylaminophenyl)-1-methoxy-3,3-dimethyl-1-butene; and 3-chlorolpropyl-2-tetrahydrofurancarboxylate will give 8-chloro-2,2-dimethyl-5-oxa-4-(2-tetrahydrofuryl)-3-octene.

EXAMPLE 2

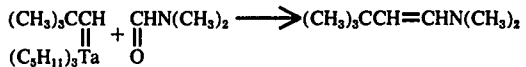

$(C_5H_{11})_3Ta=C_5H_{10}$ (0.46 g) and 0.78 ml of dimethylformamide were dissolved in about 5 ml pentane. The solution changed from orange to orange-yellow, and a white solid precipitated. After standing overnight at room temperature, the mixture was filtered, and an additional 0.78 ml of dimethylformamide was added to the filtrate. The color lightened further, and a small additional amount of white solid precipitated. The solid was separated by filtration, and the filtrate was evaporated to about 1 ml and analyzed by gas chromatography and mass spectroscopy, which showed that N,N,3,3-tetramethyl-1-butenylamine, $(CH_3)_3CCH=CHN(CH_3)_2$, had been produced. A single gas-chromatograph peak suggested that one isomer was present.

If N-formylpiperidine (pentamethyleneformamide) is used in place of dimethylformamide in essentially the foregoing procedure, 1-(3,3-dimethyl-1-butenyl)-piperidine will be formed.

EXAMPLE 3

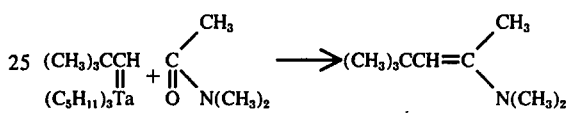

$(C_5H_{11})_3Ta=C_5H_{10}$ (2.32 g) and 0.47 ml of dimethylacetamide were dissolved in about 10 ml of pentane, and the mixture was allowed to stand at room temperature for 2 days. The solid that had precipitated was separated by filtration, another 0.47 ml of dimethylacetamide was added to the filtrate, and the solution was allowed to stand at room temperature for one more day. The additional solid that had precipitated was separated by filtration and the filtrate was evaporated, volatile materials being trapped at −196° C. Gas chromatography and mass spectroscopy showed that N,N,1,3,3-pentamethyl-1-butenylamine,

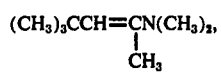

had been formed.

Other carboxamides can be used in place of dimethylacetamide to produce ethylenically unsaturated compounds by this process. For example, N,N'-diethylnonanamide will give 4-diethylamino-2,2-dimethyl-3-dodecene, N-butanoylpyrrolidine will give 2,2-dimethyl-4-(N-pyrrolidyl)-3-heptane, and N,N-dipentyl-p-toluamide will give 1-dipentylamino-1-(p-tolyl)-3,3-dimethyl-1-butene.

EXAMPLE 4

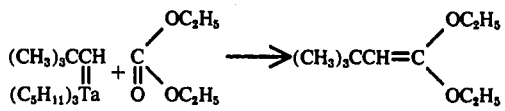

A solution of 0.464 g of trineopentyl(neopentylidene)tantalum and 0.25 g of ethyl carbonate in spectrograde hexane was kept in a sealed vessel at 100° C for about 16 hours. Volatile materials were distilled under reduced pressure. Gas-chromatographic analysis showed that 1,1-diethoxy-3,3-dimethyl-1-butene has been formed.

The products of the process of this invention are useful for removing small amounts of halogens, particularly iodine, from gaseous or liquid compositions.

EXAMPLE E

A solution of 2-ethoxy-4,4-dimethyl-2-pentene in pentane was prepared by essentially the method of Example 1. When iodine crystals were added to the solution with agitation, the purple-blue color of the iodine in pentane immediately disappeared, indicating that the iodine has been taken up by the vinyl ether.

EXAMPLE F

A solution of N,N,1,3,3-pentamethyl-1-butenylamine in pentane was prepared by essentially the method of Example 3, followed by bulb-to-bulb distillation of all volatile materials. When iodine crystals were added to the solution with agitation, the purple-blue color of the iodine in pentane immediately disappeared, indicating that the iodine had been taken up by the vinyl amine.

I claim:

1. The process of reacting a metal compound of the formula

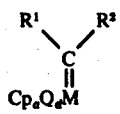

in which
Cp is a $\pi$-cyclopentadienyl group having up to one alkyl substituent of 1–10 carbons;
Q is alkyl of 1–10 carbons, aralkyl of 7–10 carbons or diarylmethyl of 13–21 carbons in which the $\beta$-carbon is not bonded to hydrogen;
M is niobium or tantalum;
$R^1$ and $R^2$ individually are hydrogen, tertiary alkyl of 4–10 carbons or aryl of 6–10 carbons;
$a$ is 0 or 2;
$d$ is 1 or 3; and
$a$ plus $d$ equals 3;
with an organic carbonyl compound of the group consisting of an ester of a carboxylic acid and an N,N-disubstituted amide of a carboxylic acid, said carbonyl compound being free of Zerewitinoff-active hydrogen and any multiple bond present, other than that in the carbonyl group, being a carbon to carbon multiple bond or a multiple bond contained in an aromatic heterocyclic ring, at a temperature in the range of 0°–250° C, in the substantial absence of oxygen and moisture, to produce an ethylenically unsaturated compound.

2. The process of claim 1 in which $a$ is 0 and $d$ is 3.
3. The process of claim 1 in which $a$ is 2 and $d$ is 1.
4. The process of claim 1 in which M is niobium.
5. The process of claim 1 in which M is tantalum.
6. The process of claim 1 in which the organic carbonyl compound is an ester of a carboxylic acid.
7. The process of claim 1 in which the organic carbonyl compound is an N,N-disubstituted amide of a carboxylic acid.
8. The process of claim 1 in which the metal compound is $(C_5H_{11})_3Ta=CHC(CH_3)_3$.
9. The process of claim 1 in which the metal compound is $(C_5H_{11})_3Ta=CH(C_6H_5)$.
10. The process of claim 1 in which the metal compound is $(C_5H_{11})_3Ta=CH_2$.
11. The process of claim 1 in which the metal compound is $(C_5H_5)_2(CH_3)Ta=CH_2$.
12. The process of claim 1 in which the metal compound is $(C_5H_{11})_3Nb=CHC(CH_3)_3$.

* * * * *